United States Patent
Gomez-Llorens

(10) Patent No.: US 12,171,663 B2
(45) Date of Patent: Dec. 24, 2024

(54) PROSTHETIC SYSTEM WITH MOTORIZED HYDRAULIC PUMP DESIGNED TO CONTROL THE INFLATION OF AN INFLATABLE ELEMENT

(71) Applicant: ZEPHYR SURGICAL IMPLANTS, Saint-Brice-Courcelles (FR)

(72) Inventor: Christophe Gomez-Llorens, Saint-Brice-Courcelles (FR)

(73) Assignee: ZEPHYR SURGICAL IMPLANTS, Saint-Brice-Courcelles (FR)

( * ) Notice: Subject to any disclaimer, the term of this patent is extended or adjusted under 35 U.S.C. 154(b) by 579 days.

(21) Appl. No.: 17/434,924

(22) PCT Filed: Mar. 20, 2020

(86) PCT No.: PCT/FR2020/050606
§ 371 (c)(1),
(2) Date: Aug. 30, 2021

(87) PCT Pub. No.: WO2020/201660
PCT Pub. Date: Oct. 8, 2020

(65) Prior Publication Data
US 2022/0125589 A1 Apr. 28, 2022

(30) Foreign Application Priority Data
Apr. 2, 2019 (FR) .................. 19 03527

(51) Int. Cl.
*A61F 2/26* (2006.01)
*A61F 2/48* (2006.01)
(52) U.S. Cl.
CPC ............ *A61F 2/26* (2013.01); *A61F 2/484* (2021.08); *A61F 2250/0001* (2013.01); *A61F 2250/0003* (2013.01)

(58) Field of Classification Search
CPC .... A61F 2/26; A61F 2/48; A61F 2/482; A61F 2/484; A61F 2250/001; A61F 2250/003
See application file for complete search history.

(56) References Cited

U.S. PATENT DOCUMENTS 5,344,388 A * 9/1994 Maxwell .................. A61F 2/26
600/40
5,823,991 A * 10/1998 Shim ......................... A61F 5/41
604/48

(Continued)

FOREIGN PATENT DOCUMENTS

| EP | 1 255 514 B1 | 4/2006 |
| WO | 01/47439 A2 | 7/2001 |
| WO | 2009/094431 A2 | 7/2009 |

OTHER PUBLICATIONS

International Search Report, dated Sep. 14, 2020, corresponding to PCT/FR2020/050606.

*Primary Examiner* — Samuel G Gilbert
(74) *Attorney, Agent, or Firm* — LADAS & PARRY LLP; Malcolm J. MacDonald, Esq.

(57) ABSTRACT

The invention relates to a prosthetic system including;
an implanted device including:
at least one inflatable element (1) that can be inflated in response to a pressure of a fluid;
a tank (2) for the fluid in communication with the inflatable element;
a sealed case (3) in which is mounted a motor-driven pump supplied with energy by a wireless energy transfer system, part of which (30) is mounted in the case, this pump being in communication on the one hand with the inflatable element via a one-way discharge obturator and on the other hand with the tank via a one-way suction obturator;
a manual command for deflating the inflatable element (1) acting simultaneously on the one-way suction and discharge obturators;

(Continued)

the control case (B) integrating another part of the energy transfer system and ensuring the control of the operation of the energy transfer system.

9 Claims, 4 Drawing Sheets

(56) References Cited

U.S. PATENT DOCUMENTS

| | | |
|---|---|---|
| 2007/0142700 A1 | 6/2007 | Fogarty et al. |
| 2008/0114202 A1* | 5/2008 | Kuyava .................... A61F 2/26 600/38 |
| 2011/0015738 A1* | 1/2011 | Vaingast ................ A61F 2/004 623/14.13 |
| 2013/0324793 A1* | 12/2013 | Derus ....................... A61F 2/26 600/40 |
| 2017/0079760 A1* | 3/2017 | Newman ................... A61F 2/26 |
| 2019/0178409 A1* | 6/2019 | Kurz .................... F16K 27/029 |

* cited by examiner

[Fig. 1]
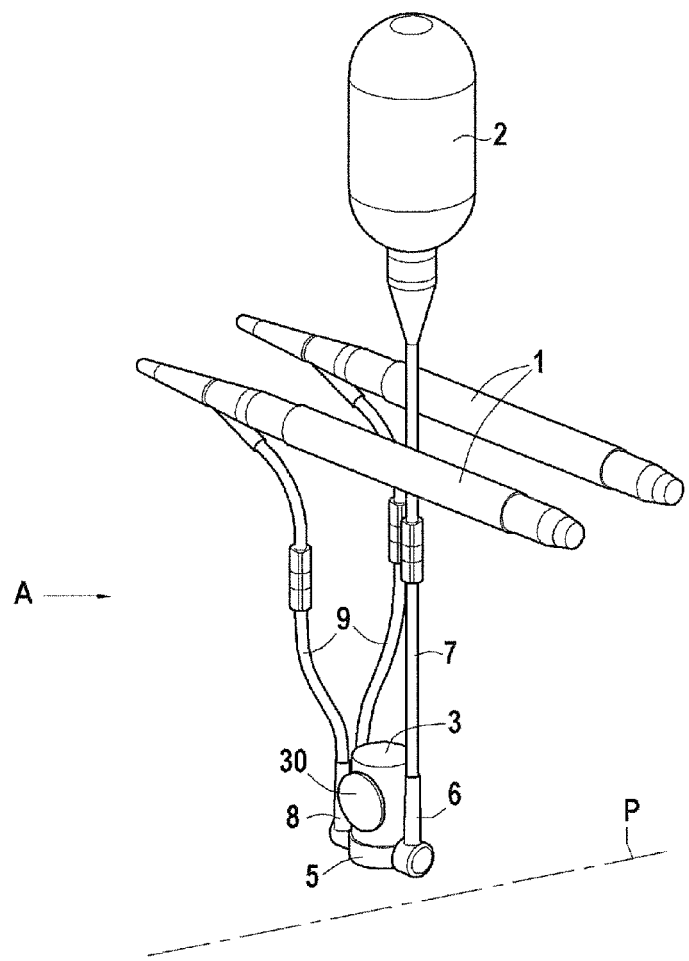
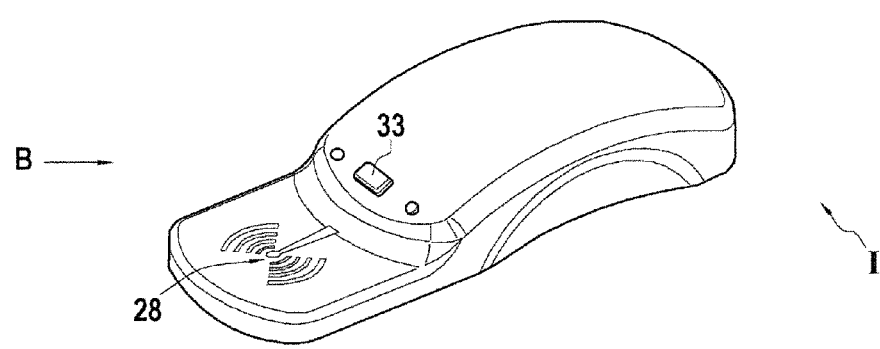

[Fig. 2]
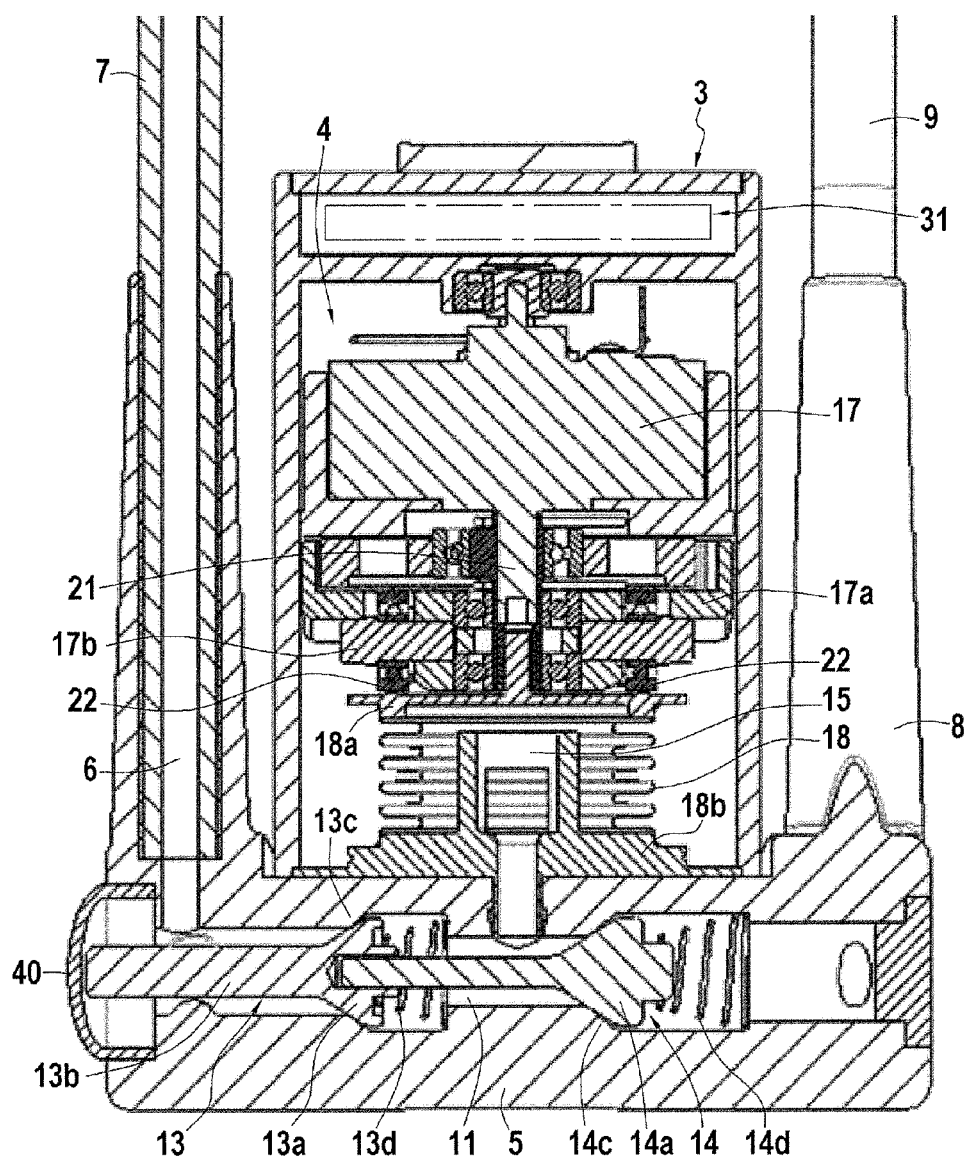

[Fig. 3]
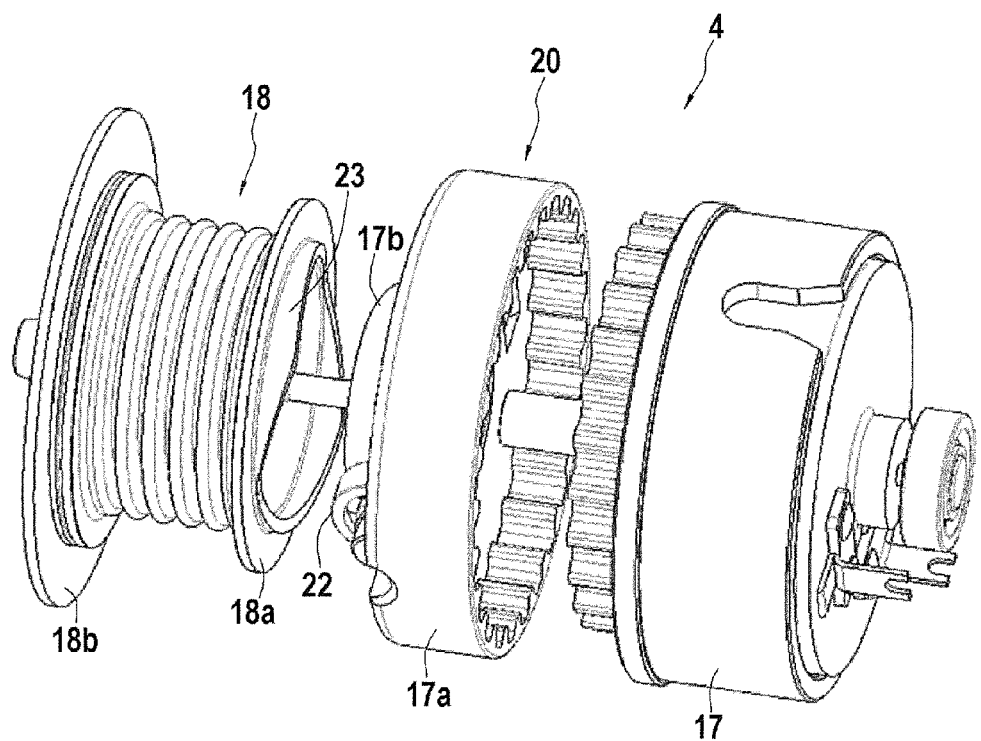

[Fig. 4]
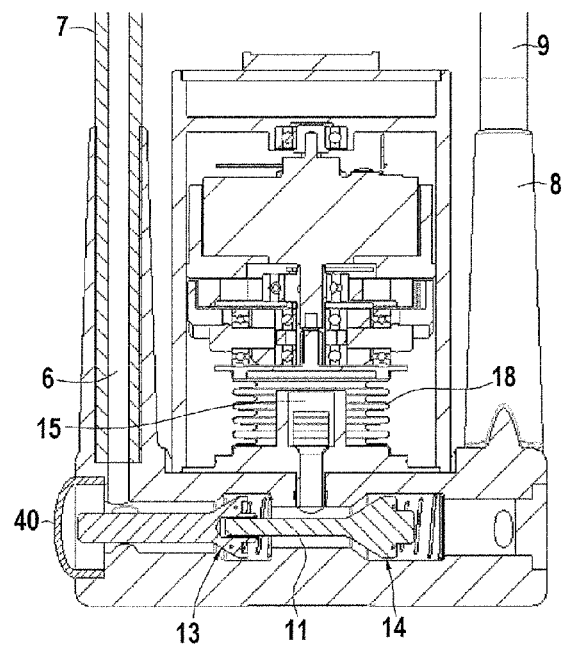
[Fig. 5]
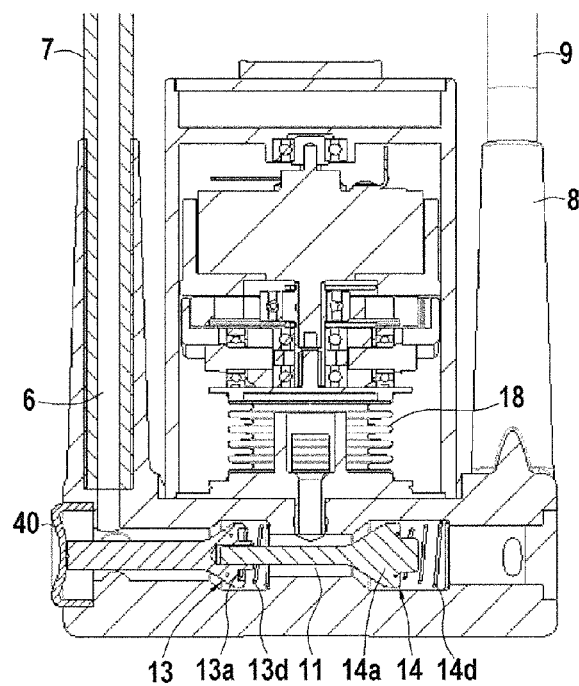

PROSTHETIC SYSTEM WITH MOTORIZED HYDRAULIC PUMP DESIGNED TO CONTROL THE INFLATION OF AN INFLATABLE ELEMENT

TECHNICAL FIELD

The present invention relates to the technical field of prosthetic or surgical implant systems with a motor-driven hydraulic pump, adapted to monitor the inflation of an inflatable element that can be inflated in response to a pressure of a fluid. More specifically, the object of the invention relates to prosthetic or surgical implant systems with a motor-driven hydraulic pump with a wireless energy transfer.

The present invention finds a preferred application for a penile implant to create an erection. The present invention finds other applications to constitute a sphincter in the general sense such as an esophageal sphincter or a gastric band or a urinary or anal sphincter.

PRIOR ART

In the technical field of prosthetic systems intended to combat male impotence, the prior art has proposed various prosthetic solutions. For example, documents EP 1 255 514 and WO 01/47439, WO 2009/094431 describe different variants of embodiment of a prosthetic system including a device implanted in the body of a patient and a control case external to the patient's body and integrating an energy transfer system. For example, the device implanted in the patient's body includes an inflatable penile implant that can be inflated in response to a pressure of a fluid contained in a tank and moved by means of a motor-driven pump supplied with energy by the wireless energy transfer system. Such a system also includes a device implantable in the patient to ensure deflation of the penile implant. It appears that such a system does not offer complete safety in particular with regard to the operation of deflating the implant. In addition, the device implanted in the patient includes different functions that do not allow them to be integrated into a space-saving case.

It is also known from document US 2007/142700 a prosthetic system with an implanted device comprising at least one inflatable element that can be inflated in response to a pressure of a fluid, in communication with a tank containing this fluid and a pump ensuring the circulation of the fluid. The implanted system requires in particular for the inflation action a mechanical action of the user on a manual pump. The implementation of such a system proves to be difficult in practice for some patients.

The present invention aims to overcome the drawbacks of the prior devices by proposing a new prosthetic system with a motor-driven hydraulic pump, adapted to monitor the inflation of an inflatable element, such a system having complete operating safety for the operations of inflating as well as for the operations of deflating the inflatable element.

Another object of the invention is to propose a new prosthetic system whose device implanted in the body of a patient is designed to have a limited space requirement.

DISCLOSURE OF THE INVENTION

To achieve such an objective, the object of the invention is a hydraulic prosthetic system including a device implanted in the body of a patient and a control case outside the patient's body;

the implanted device including:
 at least one inflatable element that can be inflated in response to a pressure of a fluid;
 a tank for the fluid in communication with the inflatable element;
 a sealed case in which is mounted a motor-driven pump driven by an electric motor supplied with energy by a wireless energy transfer system, part of which is mounted in the case, this pump being in communication on the one hand with the inflatable element via a one-way discharge obturator and on the other hand with the tank via a one-way suction obturator, the pump ensuring only the circulation of the fluid from the tank to the inflatable element to ensure its inflation;
 a manual command for deflating the inflatable element accessible from outside the sealed case and acting on the one-way suction obturator and on the one-way discharge obturator to open the communication between the inflatable element and the tank during of its manual actuation;
the control case integrating another part of the energy transfer system and ensuring the control of the operation of the energy transfer system.

The system according to the invention can advantageously be implemented with either of the following additional characteristics:
 the motor-driven pump includes a bellows delimiting a chamber for the fluid whose volume varies under the action of the electric motor, this chamber communicating with the inflatable element via the one-way discharge obturator and with the tank via the one-way suction obturator;
 the electric motor acts on the bellows via a system for transforming the rotational movement of the electric motor into a translational movement ensuring the compression and the expansion of the chamber for the fluid;
 the system for transforming the rotational movement of the electric motor into a translational movement includes a set of rollers driven in rotation by the rotor of the electric motor and cooperating with a cam fixed to the bellows;
 each one-way suction and discharge obturator is elastically returned to its closed rest position;
 each one-way suction and discharge obturator includes a valve biased by a spring to bear on a seat presented by the case, the valves being carried by an actuation rod, one free end of which is accessible from outside the case to constitute the manual command for deflating the inflatable element;
 the wireless energy transfer system includes a transmitting antenna integrated into the control case and a receiving antenna mounted in the sealed case and connected to an electronic card for conversion into a direct current supplying the electric motor;
 the control case includes a button for activating the wireless energy transfer system and a timing of the operation of the wireless energy transfer system after a determined duration of transmission;
 at least one inflatable element is a penile implant.

BRIEF DESCRIPTION OF THE DRAWINGS

FIG. 1 is a perspective view illustrating an exemplary embodiment of a penile implant prosthetic system.

FIG. 2 is an elevational sectional view showing a case integrating a motor-driven pump forming part of the prosthetic system in accordance with the invention.

FIG. 3 is an exploded perspective view showing a preferred exemplary embodiment of the motor-driven pump mounted in the case illustrated in FIG. 2.

FIG. 4 is an elevational sectional view similar to FIG. 2 and showing the one-way suction and discharge obturators of the pump, occupying an open position.

FIG. 5 is a sectional elevational view of the case similar to FIG. 2 and showing the manual command for deflating the inflatable element in the deflation position.

DESCRIPTION OF THE EMBODIMENTS

As seen more specifically in FIG. 1, the object of the invention relates to a prosthetic or surgical implant system I with a motor-driven hydraulic pump with wireless energy transfer. This prosthetic system I includes a device A intended to be implanted in the patient's body and a control case B outside the patient's body. A dashed dotted line P schematizes the patient's skin to show that the device A is implanted in the patient's body while the control case B remains outside the patient's body.

The implanted device A includes at least one and in the illustrated example, two inflatable elements 1 that can be inflated in response to a pressure of a fluid. According to this preferred exemplary embodiment, the prosthetic system 1 aims to create a penile implant in order to create an erection. According to this application, the two inflatable elements 1 are each in the form of an elongated body intended to be placed in the cavernous bodies of the penis of a man and intended to occupy a straight erection position during the inflation of the inflatable elements 1 and a folded position when the inflatable elements 1 are deflated.

Of course, the inflatable element 1 can have different shapes depending on the intended applications. Thus, the inflatable element 1 may be in the form of a cuff able to surround a member provided with an internal passage intended to be closed or opened by constriction by this inflatable element. For example, this inflatable element can be an esophageal sphincter, a gastric band or a urinary or anal sphincter.

The implanted device A also includes a tank 2 for the fluid, connected to be in communication with the inflatable elements 1. The implanted device A also includes a sealed case 3 in which is mounted a motor-driven pump 4 designed to ensure the circulation of the fluid only from the tank 2 to the inflatable elements 1 (FIG. 2). This case 3 which has a sealed nature includes a pump head 5 provided on one side with a tubing 6 for connection via a pipe 7 to the tank 2 and on the other side with a tubing 8 for communication via ducts 9 to each inflatable element 1.

As seen more specifically in FIG. 2, the head of the pump 5 includes a circulation duct 11 for the fluid communicating on one side with the tubing 6 for connection to the tank 2 and on the other side with the tubing 8 for communication with the inflatable elements 1. The duct 11 is arranged in the pump head 5 by being equipped with a one-way suction obturator 13 disposed between the motor-driven pump 4 and the tubing 6 for connection with the tank 2. The duct 11 is also equipped with a one-way discharge obturator 14 interposed between the motor-driven pump 4 and the tubing 8 for communication with the inflatable elements 1.

As seen in the drawings, each one-way suction 13 and discharge 14 obturator is elastically returned to its closed rest position. According to one preferred variant of embodiment, the one-way suction obturator 13 includes a valve 13a carried by a rod 13b mounted inside the duct 11. The valve 13a is intended to cooperate under the action of a return spring 13d, with a seat 13c arranged in the pump head 5. Likewise, the one-way discharge obturator 14 includes a valve 14a carried by the rod 13b and intended to cooperate with a seat 14c arranged in the head of the pump 5. The valve 14a is biased to bear on the seat 14c by a return spring 14d.

The duct 11 communicates between the one-way suction obturator 13 and the one-way discharge obturator 14, with a chamber 15 for the fluid whose volume varies under the action of the motor-driven pump 4. This chamber 15 thus communicates with the inflatable elements 1 via the one-way discharge obturator 14 and with the tank 2, via the one-way suction obturator 13. The motor-driven pump 4 is designed to ensure only the suction of the fluid from the tank 2 with a view to bringing it into the inflatable elements 1. Typically, the fluid used is of the physiological liquid.

According to one preferred variant of embodiment illustrated more particularly in FIG. 3, this motor-driven pump 4 includes an electric motor 17 acting on a bellows 18 internally delimiting the chamber 15 for the variable-volume fluid. The electric motor 17 acts on the bellows 18 via a system 20 for transforming the rotational movement of the electric motor 17 into a translational movement ensuring the compression and the expansion of the bellows allowing varying the volume of the chamber 15 for the fluid. For example, the electric motor 17 is an electric gear motor including a brush direct current electric motor integrating a reduction gear driving in rotation a rotor 17a about an axis of rotation 21. It should be noted that the electric motor 17 is dimensioned not to reach the bursting pressure of the inflatable elements 1. Thus, when the inflatable element 1 has reached its inflation pressure, the motor 17 stalls in case of continuation of its operation control, the bursting pressure of the inflatable elements being three times greater than the maximum inflation pressure. There is no risk of bursting. In addition, after a predefined timing and slightly longer than the time of inflation of the inflatable elements, the power supply of the motor 17 is cut off. For example, the motor 17 has a power of 1.2 W.

The rotor 17a transmits its rotational movement to the system 20 for transforming the rotational movement of the electric motor 17 into a translational movement. This transformation system 20 includes a set of two rollers 22 driven in rotation by the rotor 17a of the electric motor and cooperating with a cam 23 fixed to the bellows. In the example illustrated, the rotor 17a includes a base plate 17b provided with the two rollers 22 disposed symmetrically on either side of the axis of rotation 21, with their rolling axes perpendicular to the axis of rotation 21 of the rotor. The rollers 22 are intended to cooperate with a path of a cam 23 arranged on a movable flange 18a of the bellows 18 having a fixed flange 18b fixed on the pump head 5. The cam 23 has a profile adapted so that the rolling of the rollers 22 on the cam path leads to the application of a symmetrical force on either side of the axis of symmetry of the bellows 18 so that the latter is compressed or expanded successively during the rotation of the rotor. This cam 23 allows, by means of the motor, creating a reciprocating compression movement of the bellows 18, and therefore a pumping movement as illustrated in FIG. 4 for which the one-way suction obturator 13 and the one-way discharge obturator 14 open. The bellows 18 has an elasticity adapted to allow the variation of the chamber 15 to ensure the pumping. The bellows 18 which is made of implantable metals ensures a sealed barrier between the hydraulic fluid and the assembly constituted by the movement transformation system 20 and the electric motor 17. The pumping is carried out without friction, only by elastic deformation of the bellows. It should be noted that the pump 4 ensures the circulation of the fluid only from the tank towards the inflatable elements 1 thanks to the configuration of the one-way suction and discharge obturators.

According to one characteristic of the invention, the electric motor 17 is supplied with energy by a wireless energy transfer system, part of which is mounted in the case 3 while another part of the energy transfer system is mounted in the control case B. According to one preferred characteristic of embodiment, the wireless energy transfer system includes a transmitting coil or antenna 28 integrated into the control case B and a receiving antenna or coil 30 mounted in the sealed case 3 implanted in the patient's body. This receiving antenna 30 is connected to an electronic card 31 mounted in the case 3 and allowing transforming the high-frequency current of the receiving antenna 30 into a direct current supplying the electric motor 17. As seen more accurately in FIG. 1, the receiving antenna 30 is mounted laterally on the case 3 to allow optimum coupling with the transmitting antenna 28. Of course, the receiving antenna 30 is sealingly mounted inside the case 3. Thus, the sealed case 3 implanted in the patient's body does not include a battery.

The control case B includes a button 33 for activating the wireless energy transfer system allowing the transfer of energy to the receiving antenna 30 mounted in the sealed case 3. Advantageously, this button 33 activates the energy transfer system as long as it is manually activated. This control case B includes a timing for the operation of the wireless energy transfer system after a determined duration of transmission. Typically, the wireless energy transfer system interrupts its transmission after continuous transmission duration, for example of 3 min, even if an action continues on the button 33.

According to one characteristic of the invention, the implanted device A includes a manual command 40 for deflating the inflatable elements 1, accessible from outside the sealed case 3. This manual command 40 acts on both the one-way suction obturator 13 and the one-way discharge obturator 14 to open the communication between the inflatable elements 1 and the tank 2. In the exemplary embodiment, the manual command 40 is performed by a deflation button arranged on the head 5 of the pump and constituted by a flexible membrane mounted to sealingly close the duct 11. This manual command 40 allows, by pressing, the actuation of the rod 13b supporting the one-way obturators 13, 14 so as to ensure their opening. Advantageously, the pressing on the manual command 40 leads to the simultaneous displacement of the one-way suction obturator 13 and of the one-way discharge obturator 14. As seen in FIG. 5, the valves 13a, 14a are moved against the springs 13d, 14d causing the valves not to cooperate any longer with their seat thus enabling the fluid to circulate from the inflatable elements 1 towards the tank 2. This manual command 40 allows a deflation without fail of the inflatable elements 1.

The operation of the hydraulic prosthetic system I in accordance with the invention follows from the description above. The control case B is brought close to the skin P of the patient above the place where the sealed case 3 is implanted. Placing the transmitting antenna 28 in the vicinity of the receiving antenna 30 allows optimizing the coupling. The actuation of the button 33 of the control case B activates the energy transfer system leading to the power supply of the motor 17 of the pump. It follows that the pump 4 ensures the transfer of the fluid from the tank 2 to the inflatable elements 1. When the inflatable elements 1 are inflated, the button 33 is released. For the deflation of the inflatable elements 1, a pressing on the manual command 40 allows simultaneously placing the one-way suction obturator 13 and the one-way discharge obturator 14 in the open position ensuring the return of the fluid into the tank 2.

The invention is not limited to the examples described and represented because various modifications can be made without departing from its scope.

The invention claimed is:

1. A hydraulic prosthetic system including a device configured to be implanted in the body of a patient and a control case configured to be disposed outside the patient's body; the implanted device including:
at least one inflatable element that is inflatable in response to a pressure of a fluid;
a tank for the fluid in communication with the inflatable element;
a sealed case mounted to a motor-driven pump driven by an electric motor supplied with energy by a wireless energy transfer system, part of which is mounted in the sealed case, this pump being in communication with the inflatable element, via a one-way discharge obturator, and with the tank via a one-way suction obturator, the pump ensuring only the circulation of the fluid from the tank to the inflatable element to ensure inflation of the inflatable element;
a manual command for deflating the inflatable element accessible from outside the sealed case, and acting on both the one-way suction obturator and on the one-way discharge obturator to simultaneously open the communication between the inflatable element and the tank during manual actuation of the tank;
the control case integrating another part of the energy transfer system and ensuring the control of the operation of the energy transfer system.

2. The system according to claim 1, wherein the motor-driven pump includes a bellows delimiting a chamber for the fluid whose volume varies under the action of the electric motor, this chamber communicating with the inflatable element via the one-way discharge obturator and with the tank via the one-way suction obturator.

3. The system according to claim 2, wherein the electric motor acts on the bellows via a system for transforming the rotational movement of the electric motor into a translational movement ensuring the compression and the expansion of the chamber for the fluid.

4. The system according to claim 3, wherein the electric motor comprises a rotor, and wherein the system for transforming the rotational movement of the electric motor into a translational movement includes a set of rollers driven in rotation by the rotor, and cooperating with a cam fixed to the bellows.

5. The system according to claim 1, each one-way suction and discharge obturator is elastically returned to a closed rest position.

6. The system according to claim 5, wherein each one-way suction and discharge obturator includes a valve biased by a spring to bear on a seat presented by the sealed case, the valves being carried by an actuation rod, one free end of the actuation rod being which is accessible from outside the case to constitute the manual command for deflating the inflatable element.

7. The system according to claim 6, wherein the wireless energy transfer system includes a transmitting antenna integrated into the control case and a receiving antenna mounted in the sealed case and connected to an electronic card for conversion into a direct current supplying the electric motor.

8. The system according to claim 1, wherein the control case includes a button for activating the wireless energy transfer system and a timing of the operation of the wireless energy transfer system after a determined duration of transmission.

9. The system according to claim 1, wherein at least one inflatable element is a penile implant.

* * * * *